United States Patent [19]
Norris

[11] Patent Number: 5,450,856
[45] Date of Patent: Sep. 19, 1995

[54] PHLEBOTOMY NEEDLE ATTACHABLE TO A VACUUM CONTAINER WITH A VENT TO PRECLUDE BLOOD FLASHBACK

[76] Inventor: Wendal A. Norris, 215 Liberty Rd., Wartburg, Tenn. 37887

[21] Appl. No.: 232,639
[22] Filed: Apr. 25, 1994
[51] Int. Cl.⁶ .............................................. A61B 5/00
[52] U.S. Cl. ................................... 128/764; 128/766
[58] Field of Search ............... 128/763, 765, 766, 770; 604/168

[56] References Cited

U.S. PATENT DOCUMENTS

| | | | |
|---|---|---|---|
| 4,416,291 | 11/1983 | Kaufman | 128/763 |
| 4,418,703 | 12/1983 | Hoch et al. | 128/763 |
| 4,444,203 | 4/1984 | Engelman | 128/763 |
| 4,886,072 | 12/1989 | Percarpio et al. | 128/763 |
| 5,098,395 | 3/1992 | Fields | 604/168 |

FOREIGN PATENT DOCUMENTS 2716774  10/1978  Germany ..................... 128/763

Primary Examiner—Max Hindenburg

[57] ABSTRACT

A phlebotomy needle attachable to a vacuum container with a vent to preclude blood flashback, comprising an outboard needle adapted to be penetrated into the vein of a patient for extracting blood. The device further including an inboard needle adapted to be received by a vacuum tube in axial alignment with the outboard needle and in fluid communication therewith for receiving blood drawn from the patient by the outboard needle. The device further including a hollow transparent bulb coupled between the needles and in axial alignment therewith.

1 Claim, 5 Drawing Sheets

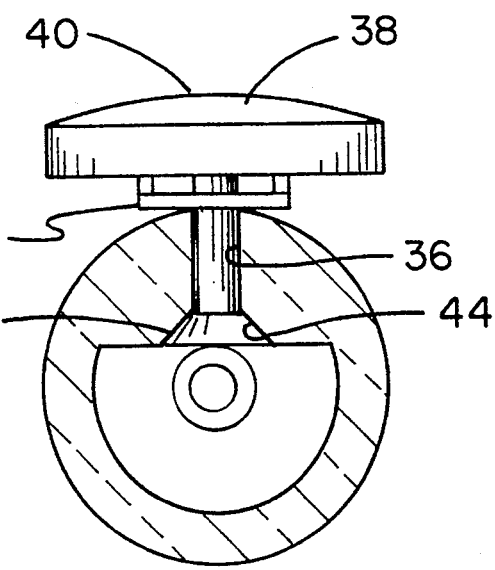
FIG. 6
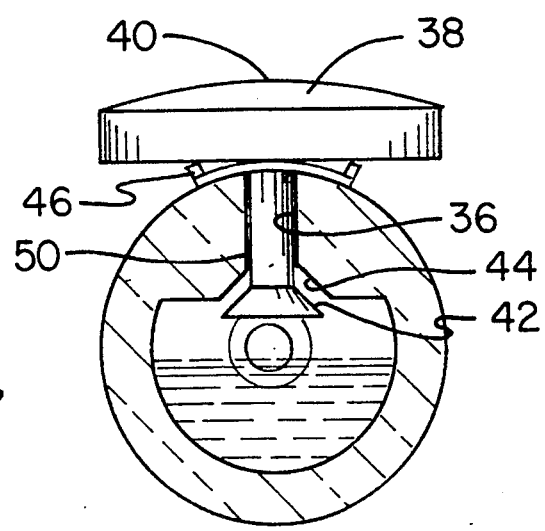
FIG. 7
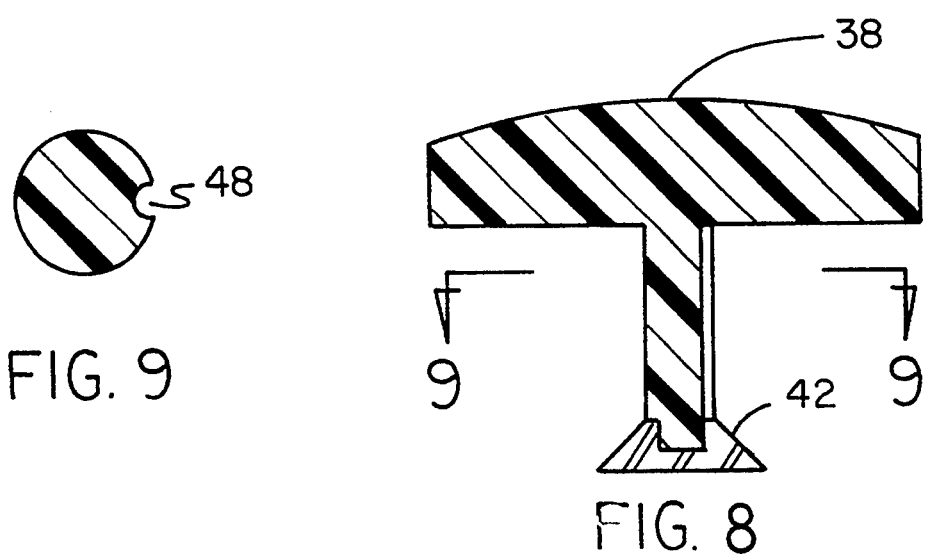
FIG. 9
FIG. 8

PHLEBOTOMY NEEDLE ATTACHABLE TO A VACUUM CONTAINER WITH A VENT TO PRECLUDE BLOOD FLASHBACK

BACKGROUND OF THE INVENTION

1. Field of the Invention

The present invention relates to a phlebotomy needle attachable to a vacuum container with a vent to preclude blood flashback and more particularly pertains to drawing blood to a vacuum container without the use of a syringe and with a vent to preclude blood flashback to exterior of the container.

2. Description of the Prior Art

The use of phlebotomy needles for drawing blood to a container is known in the prior art. More specifically, phlebotomy needles for drawing blood to a container heretofore devised and utilized for the purpose of drawing blood from a patient for testing purposes are known to consist basically of familiar, expected, and obvious structural configurations, notwithstanding the myriad of designs encompassed by the crowded prior art which has been developed for the fulfillment of countless objectives and requirements.

By way of example, U.S. Pat. No. 3,916,892 to Latham, Jr. discloses a phlebotomy needle system incorporating means to add anticoagulant and wash liquid.

U.S. Pat. No. 4,280,496 to Van Baelen discloses a phlebotomy needle assembly.

U.S. Pat. No. 4,904,242 to Kulli discloses a phlebotomy set with safety retracting needle.

U.S. Pat. No. 5,085,640 to Gibbs discloses a nonreusable medical needle apparatus.

Lastly, U.S. Pat. No. 5,178,157 to Fanlo discloses a phlebotomy device and method of use thereof.

In this respect, the phlebotomy needle attachable to a vacuum container with a vent to preclude blood flashback according to the present invention substantially departs from the conventional concepts and designs of the prior art, and in doing so provides an apparatus primarily developed for the purpose of drawing blood to a vacuum container without the use of a syringe and with a vented shield to preclude blood flashback to exterior of the container.

Therefore, it can be appreciated that there exists a continuing need for a phlebotomy needle attachable to a vacuum container with a vent to preclude blood flashback which can be used for drawing blood to a vacuum container without the use of a syringe and with a vent to preclude blood flashback to exterior of the container. In this regard, the present invention substantially fulfills this need.

SUMMARY OF THE INVENTION

In view of the foregoing disadvantages inherent in the known types of phlebotomy needles for drawing blood to a container now present in the prior art, the present invention provides an improved phlebotomy needle attachable to a vacuum container with a vent to preclude blood flashback. As such, the general purpose of the present invention, which will be described subsequently in greater detail, is to provide a new and improved phlebotomy needle attachable to a vacuum container with a vent to preclude blood flashback and method which has all the advantages of the prior art and none of the disadvantages.

To attain this, the present invention essentially comprises a new and improved phlebotomy needle attachable to a vacuum container with a vent to preclude blood flashback, comprising, in combination an outboard needle adapted to be penetrated into the vein of a patient for extracting blood. The device further including an inboard needle adapted to be received by a vacuum tube in axial alignment with the outboard needle and in fluid communication therewith for receiving blood drawn from the patient by the outboard needle. The device further including a hollow transparent bulb coupled between the needles and in axial alignment therewith, the bulb including an outboard end with a cross section adapted to receive an outboard shield for the outboard needle, the bulb having a threaded inboard end for removable attachment to a handle and, interingly thereof, a vacuum tube for receiving the blood of a patient. The device further including a button radially extending into the bulb, the button adapted to be in a normally raised orientation to preclude the flow of blood through the bulb, the button movable to a depressed orientation to relieve air and thereby to allow the flow of blood through the bulb and needles. The device further including an elastomeric shield positionable over the inboard needle adapted to relieve air and to preclude the flashback of blood. The device further including a handle of a tubular configuration and having an outboard end with internal threads adapted to be received on the threads of the bulb, the handle having an opened inboard end for the passage of the vacuum tube therein.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent of legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved phlebotomy needle attachable to a vacuum container with a vent to preclude blood flashback which have all the advantages of the prior art phlebotomy needles for drawing blood to a container and none of the disadvantages.

It is another object of the present invention to provide new and improved phlebotomy needle attachable to a vacuum container with a vent to preclude blood flashback which may be easily and efficiently manufactured and marketed.

It is further object of the present invention to provide a new and improved phlebotomy needle attachable to a vacuum container with a vent to preclude blood flashback which are of durable and reliable constructions.

An even further object of the present invention is to provide a new and improved phlebotomy needle attachable to a vacuum container with a vent to preclude blood flashback which are susceptible of a low cost of manufacture with regard to both materials and labor, and which accordingly are then susceptible of low prices of sale to the consuming public, thereby making such phlebotomy needle attachable to a vacuum container with a vent to preclude blood flashback economically available to the buying public.

Still yet another object of the present invention is to provide a new and improved phlebotomy needle attachable to a vacuum container with a vent to preclude blood flashback which provide in the apparatuses and methods of the prior art some of the advantages thereof, while simultaneously overcoming some of the disadvantages normally associated therewith.

Even still another object of the present invention is to draw blood to a vacuum container without the use of a syringe and with a vented shield to preclude blood flashback to exterior of the container.

Lastly, it is an object of the present invention to provide a new and improved phlebotomy needle attachable to a vacuum container with a vent to preclude blood flashback, comprising an outboard needle adapted to be penetrated into the vein of a patient for extracting blood. The device further including an inboard needle adapted to be received by a vacuum tube in axial alignment with the outboard needle and in fluid communication therewith for receiving blood drawn from the patient by the outboard needle. The device further including a hollow transparent bulb coupled between the needles and in axial alignment therewith.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 6 is a cross sectional view of the phlebotomy needle taken along line 6—6 of FIG. 5.

FIG. 7 is a cross sectional view similar to FIG. 6 but illustrating the flow of blood therethrough.

FIG. 8 is a cross sectional view of the button employed in the phlebotomy needle of the prior figures.

FIG. 9 is a cross sectional view taken along line 9—9 of FIG. 8.

The same reference numerals refer to the same parts through the various figures.

DESCRIPTION OF THE PREFERRED EMBODIMENT

Figure 1:
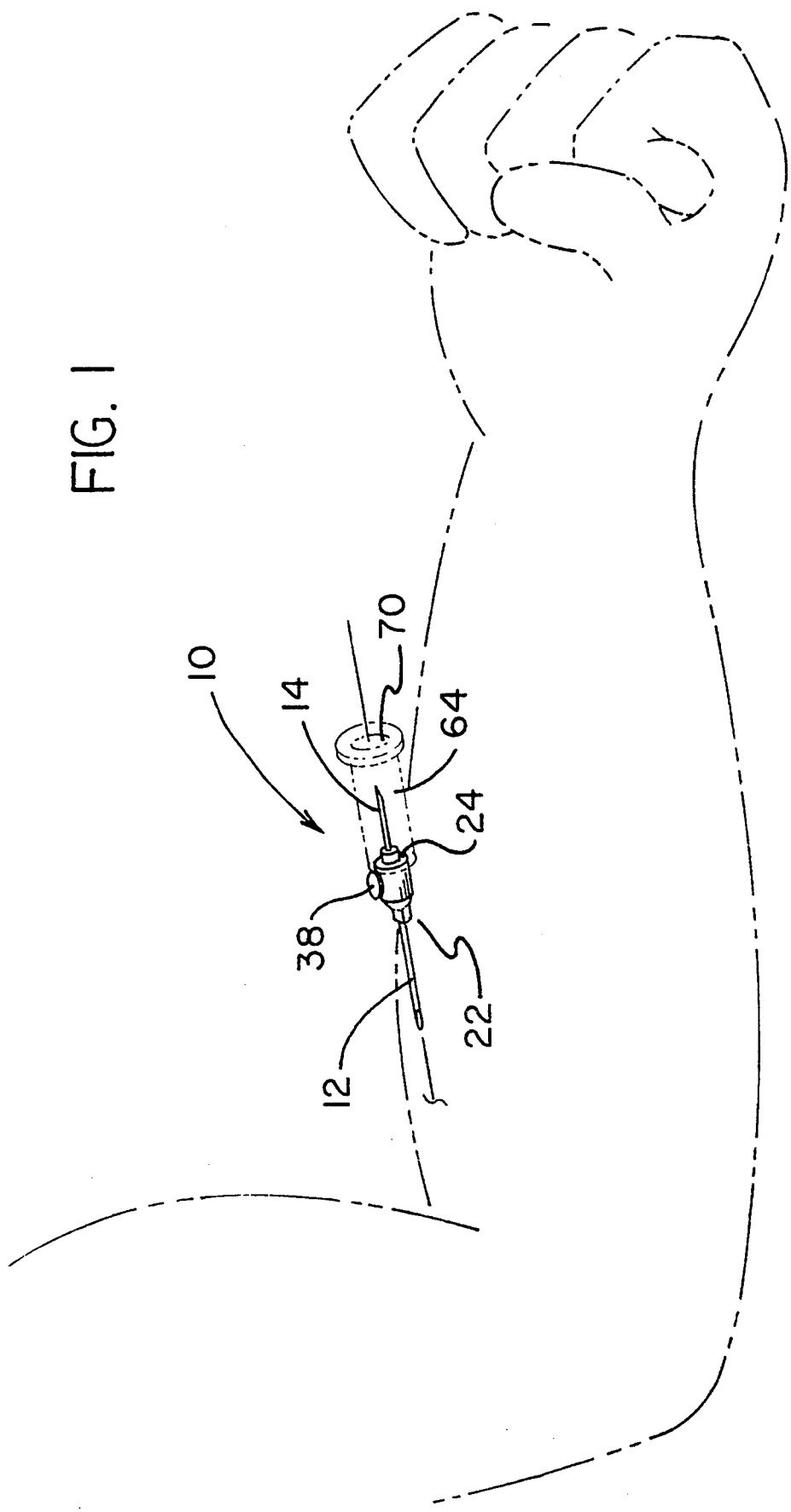
FIG. 1 is a perspective view of the preferred embodiment of the new and improved phlebotomy needle attachable to a vacuum container with a vent to preclude blood flashback constructed in accordance with the principles of the present invention.
Figure 2:
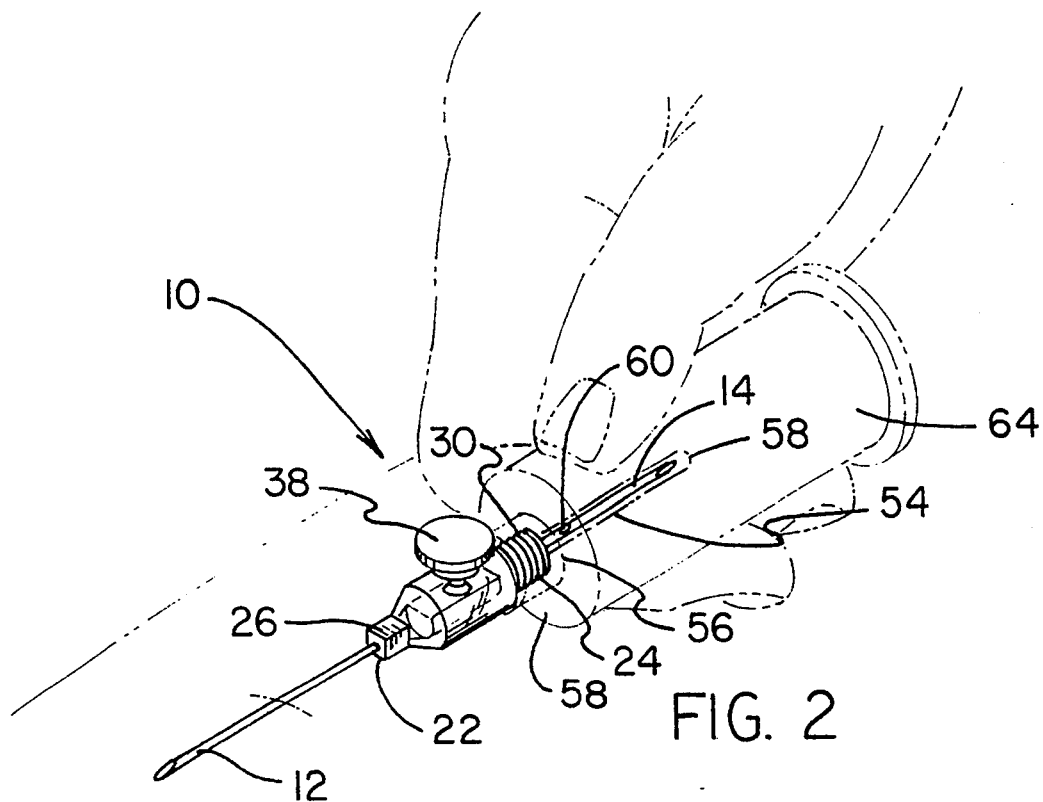
FIG. 2 is a perspective view of the phlebotomy needle shown in FIG. 1.
Figure 3:
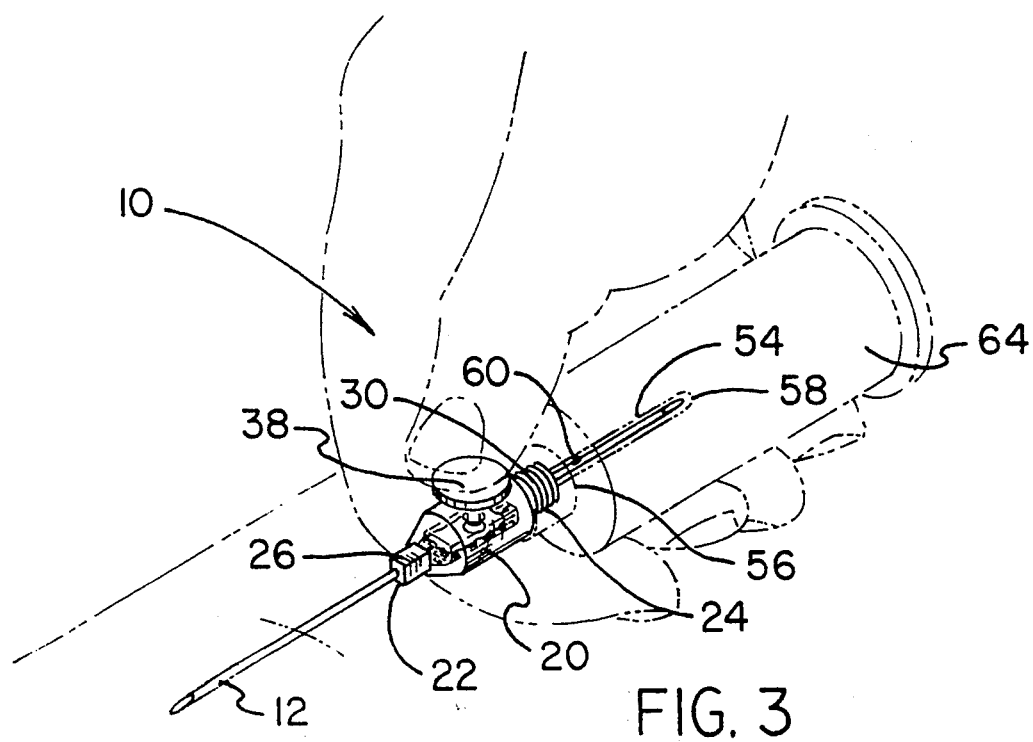
FIG. 3 is a perspective view of the phlebotomy needle similar to FIG. 2 but illustrating the button depressed for the flow of blood.
Figure 4:
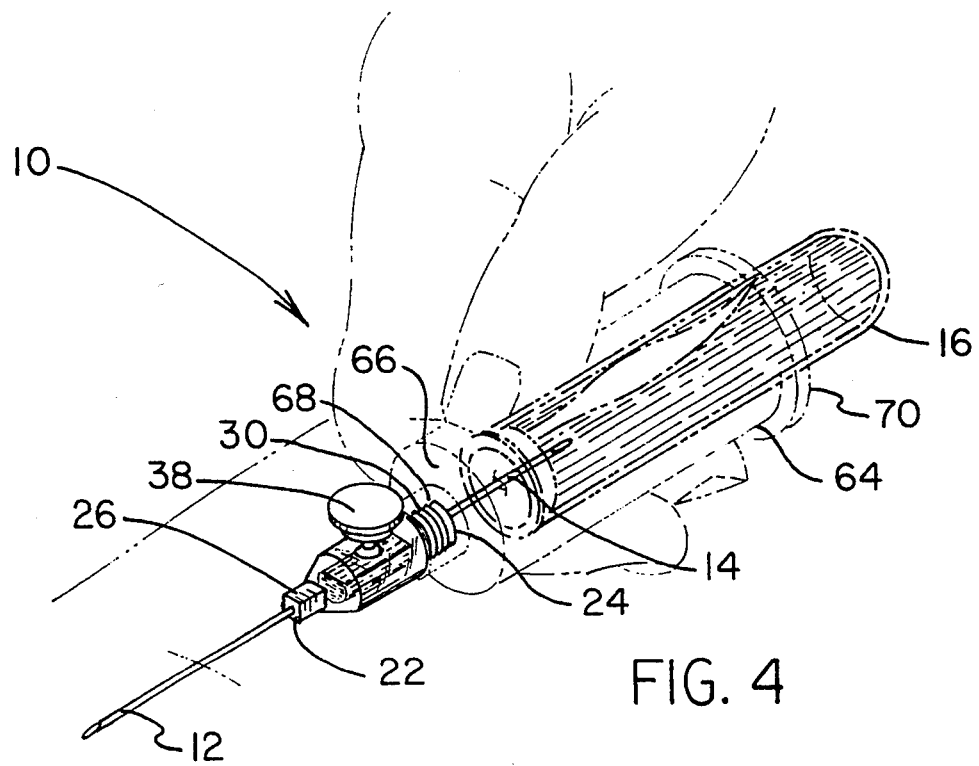
FIG. 4 is a perspective view of the phlebotomy needle similar to FIGS. 2 and 3 illustrating the blood being received in the vacuum container.
Figure 5:
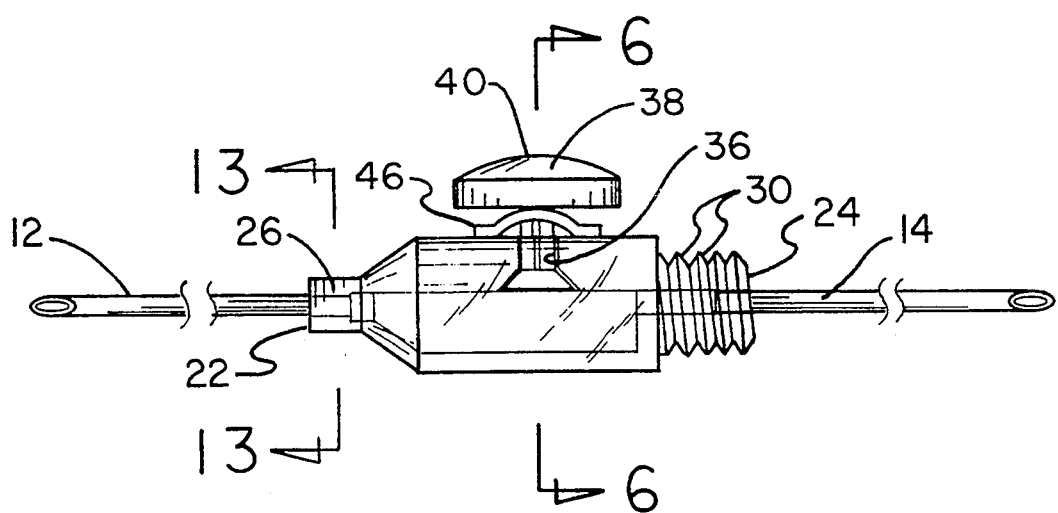
FIG. 5 is a side elevational view of the phlebotomy needle of the prior Figures.
Figure 11:
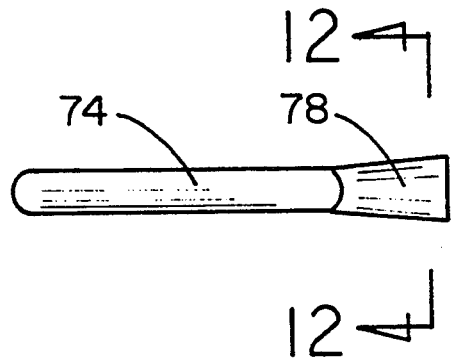
FIG. 11 is a perspective view of the shield being removed from the outboard needle.
Figure 10:
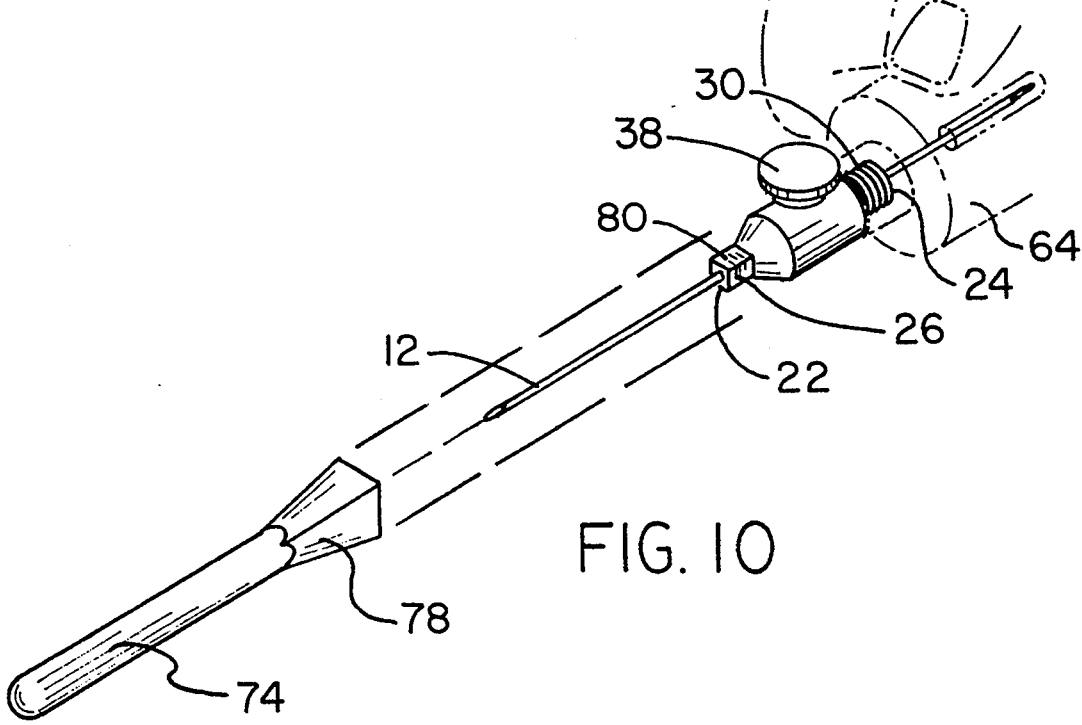
FIG. 10 is a side elevational view of the shield for the outboard needle.
Figure 12:
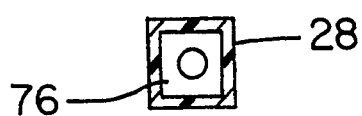
FIG. 12 is a cross sectional view taken along line 12—12 of FIG. 11.
Figure 13:
FIG. 13 is a cross sectional view of the shield taken along an intermediate point thereof.

With reference now to the drawings, and in particular to FIG. 1 thereof, the preferred embodiment of the new and improved phlebotomy needle attachable to a vacuum container with a vent to preclude blood flashback embodying the principles and concepts of the present invention and generally designated by the reference numeral 10 will be described.

The present invention the new and improved phlebotomy needle attachable to a vacuum container with a vent to preclude blood flashback is comprised of a plurality of component elements. In their broadest context, such elements include an outboard needle, an inboard needle, a bulb therebetween, a button formed in the bulb for venting purposes, a shield over the inboard needle for venting purposes and a tubular handle coupled to the inboard end of the bulb. Such components are individually configured and correlated with respect to each other so as to attain tile desired objective.

More specifically, the present invention is a system 10 which includes an outboard needle 12. The outboard needle is of a hollow construction with a pointed outboard end for penetrating the vain of a patient. In this manner, blood may be extracted for subsequent testing purposes.

The system 10 also includes an inboard needle 14. Such needle is adapted to be received within a conventional vacuum tube 16. The inboard needle is positionable in axial alignment with the outboard needle. It is also adapted to be in fluid communication therewith. The inboard needle functions for receiving blood drawn from the patient by the outboard needle and depositing such blood within a vacuum tube.

Centrally located between the two needles is a bulb 20. Such bulb is hollow and is fabricated of a transparent material, preferably plastic. The bulb has an outboard end 22 coupled to the inboard end of the outboard needle. The bulb also has an inboard end 24 coupled to the outboard end of the inboard needle. The bulb is configured in axial alignment with such needles. The bulb has at its outboard end a cross section 26 adapted to receive an outboard shield 28 for the outboard needle. On the inboard end, the bulb is formed with external threads 30. Such threads are for the removable attachment to a handle as will be described. In addition, the handle is hollow with open ends for the receiving of a vacuum tube 32 therein. The vacuum tube is for receiving the blood of a patient when coupled with respect to the inboard needle.

When the outboard needle is penetrated into the vain of a patient, there is a tendency of the blood from the vain to move through the needles. Such, however, is precluded because of the presence of air within the needles and the bulb. Blood can be allowed to flow only if such air is vented. To effect such venting, a radial aperture 36 is formed in the bulb. Within such aperture is a button 38. The button has an exterior end 40 for being depressed by the health care provider. The button has an interior end 42 adapted to provide an air tight sealing surface with a flared radially interior surface 44 of the bulb. A spring 46 holds the button upwardly to thereby seal the aperture. Note FIG. 6. When, however, the button is depressed against the action of the spring, the interior end of the button moves away from its associated surface to allow air to be vented and blood to flow. Note FIG. 7. In this manner, the button is adapted to be in a normally raised position to preclude the flow of blood through the bulb. The button is then moveable to a depressed orientation to relieve air and thereby to allow the flow of blood through the bulb and needles. Such a capability is important since it would be wasteful to insert a vacuum tube on the inboard needle if proper penetration had not been first attained. Such proper penetration is verified by the relieving of the air from the bulb and verifying it by visual observation within the transparent bulb. An axial recess 48 is formed in the portion of the button along the intermediate extent. Such recess is adapted to ride within a similarly configured axial projection 50 formed in the radial aperture through the bulb. This allows for proper axial sliding of the button with respect to the bulb.

In addition to the button, a supplemental venting is permitted through an elastomeric shield 54. Such shield may be used in addition to or, as an alternative to the button for acting purposes. The shield is a cylindrical resilient member having an open outboard end 56 and a closed inboard end 58. It also has a vent hole 60. The vent hole is located adjacent to the outboard end. The shield is spaced slightly from tile inboard needle along its length. In this manner, when a vain is penetrated, the blood will flow into the vacuum tube but air will be vented through the radial aperture of the shield. When positioning a vacuum tube over the inboard needle, the shield will be penetrated by the needle at the inboard end and will be urged upwardly toward the bulb. When, however, the vacuum tube is removed, the resilience of the shield will urge it back to its original orientation but with an aperture at the previously closed end.

The next component of the system 10 is the handle 64. The handle is of a tubular construction from a transparent material, preferably plastic. Glass could be utilized. Such handle has an outboard end 66 with internal threads 68 adapted to be received on the threads of the bulb. The handle has an opened inboard end 70. this opening is for the passage of the vacuum tube therein.

The last component of the system 10 is an outboard shield 74. The outboard shield is adapted to retain the outboard needle sanitary during storage, operation and use. It also serves as a safety device to preclude inadvertent injury to the patient or health care provider. Such shield has a tubular interior hollow cross section 76 along the majority of the length for shielding the needle. It also has, at its inboard end, a rectangular cross section 78 for positioning over a similarly shaped cross section 80 at the outboard end of the bulb.

The present invention greatly simplifies the performance of a phlebotomy. A phlebotomy is a medical term for a procedure which is performed by doctors. It is similar to a venesection which refers to the opening of a vein in the body to remove blood. A phlebotomy, however, refers to the therapeutic letting of blood, such as for reducing the viscosity of the blood in a patient who has polycythemia which has caused a rise in blood pressure.

The present invention consists of a venipuncture needle that directs the blood into a clear bulb which has a needle at the opposite end. This can then be inserted into the vacuum tube which is used in such procedures. A screw thread is provided behind the clear bulb so it can be threaded into a holder which contains the vacuum tube. This unit is made in one piece, making it very easy to put the assembly together. When penetration is made into the vein the doctor can see the blood accumulate in the bulb before the vacuum tube is attached. It assures the doctor that a good penetration has been made. Syringes are thereby eliminated to save some cost.

Since babies have smaller veins and geriatric patients have thinner ones, these needles can be made in several sizes that are more suited to the individual. The needles are made of stainless steel, but the bulb is clear plastic with molded threads.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by LETTERS PATENT of the United States is as follows:

1. A new and improved phlebotomy needle attachable to a vacuum container with a vent to preclude blood flashback, comprising, in combination:

an outboard needle adapted to be penetrated into the vein of a patient for extracting blood;

a inboard needle adapted to be received by a vacuum tube in axial alignment with the outboard needle and in fluid communication therewith for receiving blood drawn from the patient by the outboard needle;

a hollow transparent bulb centrally coupled between the needles and in axial alignment therewith, the bulb including an outboard end with a cross section adapted to receive an outboard shield for the outboard needle, the bulb having an external threaded inboard end for removable attachment to a handle and, interingly thereof, a vacuum tube for receiving the blood of a patient, the bulb further including a radial aperture therein with an axial projection;

a button radially extending into the bulb, the button having an exterior end for depressing and an interior end with a flared radially interior surface and an intermediate extent therebetween with an axial recess, the axial recess capable of slidable riding of the axial projection of the aperture of the bulb for proper venting of air through the aperture, the button adapted to have a spring for maintaining a normally raised orientation to preclude the flow of blood through the bulb, the button movable to a depressed orientation to receive air and thereby to allow the flow of blood through the bulb and needles;

an elastomeric shield being cylindrical in configuration having an open outboard end with a vent hole adjacent thereto and a closed inboard end, the shield being positionable over the inboard needle adapted to relieve air and to preclude the flashback of blood, the shield further capable of being penetrated by the inboard needle when the vacuum tube being urged upwardly over the inboard needle engaging the bulb; and a handle of a tubular configuration and having an outboard end with internal threads adapted to be received on the threads of the bulb, the handle having an opened inboard end for the passage of the vacuum tube therein.

* * * * *